United States Patent [19]

Crisci

[11] 4,078,696

[45] Mar. 14, 1978

[54] CONTAINERS AND CLOSURES THEREFOR

[75] Inventor: Victor Eugene Crisci, Wellsburg, W. Va.

[73] Assignee: Polysar Resins, Inc., Leominster, Mass.

[21] Appl. No.: 772,274

[22] Filed: Feb. 25, 1977

[51] Int. Cl.² .............................................. B65D 39/00
[52] U.S. Cl. ..................................... 220/308; 215/317
[58] Field of Search ............... 220/306, 308, 355, 356; 150/.5; 215/317, 321

[56] References Cited

U.S. PATENT DOCUMENTS

| 3,688,942 | 9/1972 | Mitchell et al. | 220/306 |
| 3,977,563 | 8/1976 | Holt | 220/306 |

Primary Examiner—George T. Hall
Attorney, Agent, or Firm—Stevens, Davis, Miller & Mosher

[57] ABSTRACT

A closure and container in which the closure has an axial flange which cooperates with the container to lock the closure in closed position, the closure also having an annular recess accommodating a resilient seal for sealing against the container rim. The seal projects from the recess before assembly of closure to container. During assembly, the container compresses the seal into the recess until in the fully closed position, the container engages a seating surface upon the closure, at which point the seal is only partially compressed.

2 Claims, 3 Drawing Figures

CONTAINERS AND CLOSURES THEREFOR

This invention relates to containers and closures therefor and is concerned particularly with the seating of closures upon container rims and the sealing effect provided between closures and container rims.

In closure and container constructions in which effective sealing between the two components is of utmost importance, separate annular seals may be provided, these seals either being detachable from the closure or container or being secured in position by adhesive. To obtain a positive seal and positive seat between conventional containers and their closures while preventing movement of the closures upon the containers, it is necessary fully to compress the seals by the closure force between the two components. However, after the full closure force has been applied for a period of time, mechanical hysteresis takes effect and a seal tends to become set in its compressed state thereby reducing the resilient reactive force applied against the container so that the sealing effect is at least partially destroyed. Further, although a seal may be sealing efficiently, it may have set at least partly towards its compressed state in which it is faithfully shaped complementarily to any imperfections against a container or closure seat. In such a case, once the closure has been removed, because it may never be possible for it to be replaced in exactly the same circumferential position upon its container, leakage may take place. One way of overcoming the disadvantage caused by mechanical hysteresis at full compression of the seals, is to reduce the amount of closure force applied across the seals. However, with conventional constructions the reduction of the compressive force on the seals is impractical as this would lead to a less positive attachment of the closures to the containers thus resulting in sloppiness of fit which is not a desirable characteristic of containers especially those of large capacity.

According to one aspect of the present invention, a closure for a container comprises a container closure portion surrounded by an annular rim portion, the rim portion having an axial flange, a container seating surface and an annular recess formed with an opening, and the seating surface facing axially along the flange, the axial flange having a radially extending locking means for locking engagement with a container and for holding the container compressively against the seating surface, and the recess being provided to accommodate a resilient seal sealingly to engage a container when the container is held compressively against said seating surface. Preferably, the recess has its opening facing axially along the flange so that compression of the seal takes place in the axial direction when the container is held in position by the locking projection. Alternatively, the opening may face in a radial direction so that the seal slidingly engages against an axially extending surface of the container during assembly of the container and closure.

According to another aspect of the present invention, a closure for a container comprises a container closure portion surrounded by an annular rim portion, the rim portion having an axial flange, a container seating surface and an annular recess formed with an opening, the seating surface and the opening to the recess both facing axially along the flange, and the recess accommodating a resilient seal which in an unsealing condition projects outwardly from the recess opening, the projecting part of the seal being resiliently compressible towards the recess, and the axial flange having a radially extending locking means for locking engagement with a container and for holding the container compressively against the seating surface with the container resiliently compressing the projecting part of the seal towards the recess.

In an assembly of container and closure, it is an important feature according to the invention that a positive seat is provided between closure and container while the resilient seal is held in a partially compressed state so that the seal takes little, if any, of the closure forces between container and closure. Accordingly, in an assembly of container and closure according to another feature of the invention, the container has a rim and the closure comprises a container closure portion extending across an opening of the container and an annular rim portion surrounding the closure portion, the rim portion having an axial flange and a container seating surface facing axially along the flange, the closure and container each comprising parts of a locking device, and the closure being sealingly closed upon the container rim with the parts of the locking device cooperating to retain the closure upon the container and holding the container in positive compressive engagement against the seating surface so that the closure forces are transmitted through the seating surface, and the container and closure defining between them an annular chamber containing a resilient seal, the seal being in a partially compressed state and sealingly engaging both the container and the closure.

The seal may be contained between telescoping parts of the container and closure whereby it slidingly engages a container wall during assembly of the container and closure together. It is to be preferred, however, that the seal held by the closure lies in an annular recess formed with an opening and the opening faces in the same direction as the seating surface, i.e. axially along the flange. In a preferred construction, the container seating surface is contiguous with the opening to the recess and lies radially outside the opening to the recess.

One embodiment of the invention will now be described, by way of example, with reference to the accompanying drawings in which.

Figure 1:
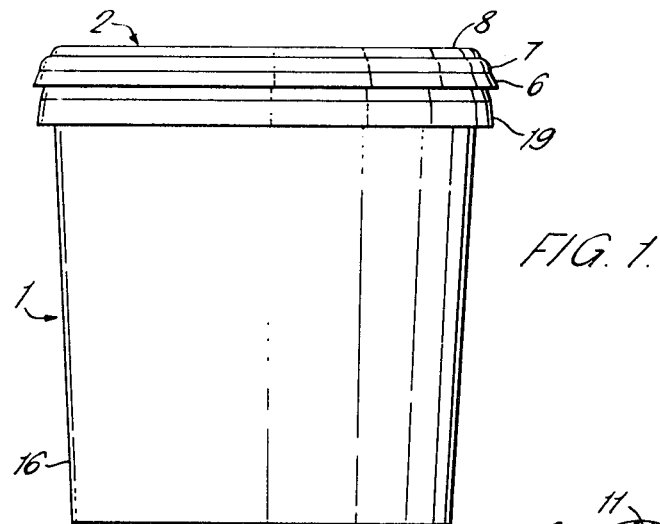
FIG. 1 is a side elevational view of the container.

In the embodiment as shown in the drawings, a container and closure generally indicated by numerals 1 and 2 are both injection moulded from a poly-alpha-olefin such as high density polyethylene although impact polypropylene may be used. Alternatively, other suitable materials may be used instead such as a polyvinyl halide, e.g. polyvinyl chloride or a polyvinyl aromatic, e.g. polystyrene.

Figure 3:
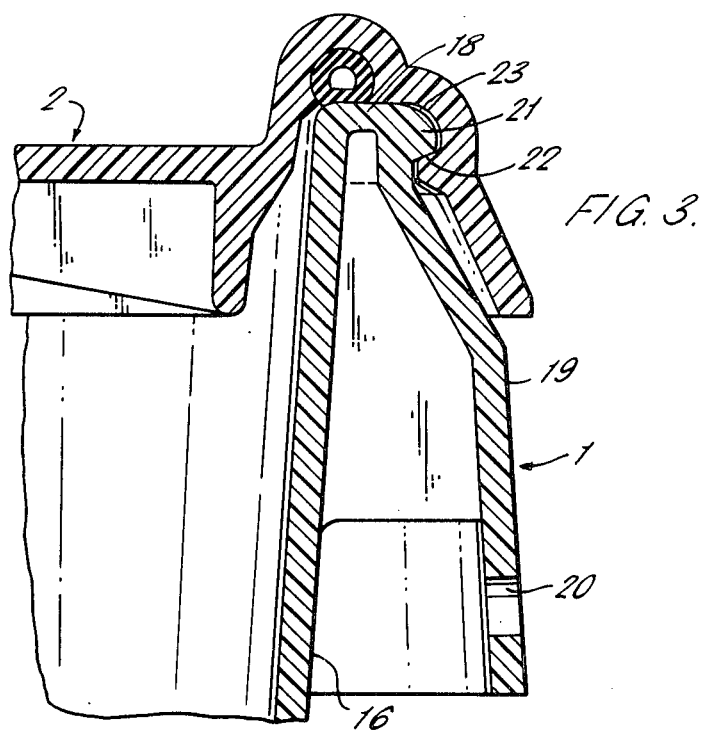
FIG. 3 is a view similar to FIG. 2 showing the closure fitted to a container.

The closure 2 is constructed with a container closure portion 3 which is of planar configuration, the closure portion being surrounded by a circular rim portion 4. The rim portion 4 is of a general 'U' shape in cross-section as shown in the Figures and comprises a radially inner wall 5 which extends in a generally axial direction and a radially outer wall 6 concentric with the inner wall and joined to it by a base 7. The 'U' rim is inverted when the closure is fitted to a container as shown in FIG. 3. The container closure portion 3 interconnects with the inner wall 5 substantially halfway along its axial depth and reinforcing ribs 3a extend from the lower end of the inner wall across the underside of the container closure portion to provide strength and rigidity to the container closure portion. As can be seen, these ribs are of tapering section towards the axis of the closure.

Figure 2:
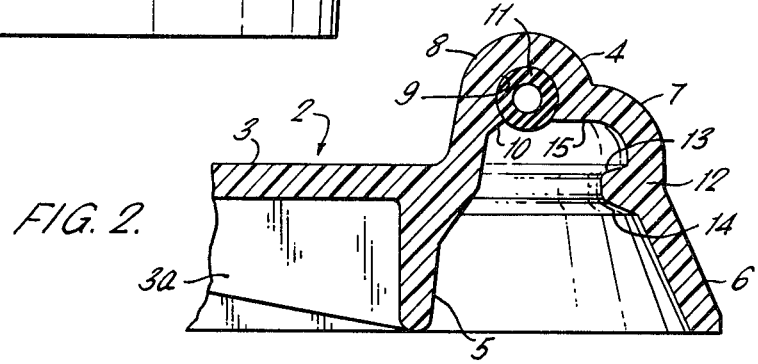
FIG. 2 is a cross-sectional view taken along the axis of the closure.

The part of the base 7 which joins onto the inner wall 5 is domed as shown at 8. The dome surrounds the base and sides of an annular recess 9 having an opening 10 into the space defined between the walls of the 'U'. The recess as shown in FIG. 2 accommodates an O-ring gasket 11 made of resilient plastics material. The gasket 11 is of substantially circular cross-section as shown in FIG. 2 and it is contained in intimate contact with the side walls and base of the recess as these are of concave configuration and merge into one another to form a smooth concave surface around the recess from one side of the opening to the other. In the uncompressed state of the O-ring, i.e. before the closure is fitted to a container rim, the O-ring projects outwardly through the opening beyond the base level of the 'U' shape of the rim as shown in FIG. 2.

The radially outer wall of the rim is provided with an annular locking projection or locking means 12 forming part of a locking device for locking the closure around the rim of the container as will be described. This locking projection extends radially inwardly from the inner surface of the wall 6 and is of conventional shape for such projections in that it has an upper surface 13 and a lower surface 14, the latter surface sloping to provide a camming action when the closure is applied to a container to cause the wall 6 to flex outwardly to enable the container rim to seat correctly into the closure.

The closure is also provided with an annular seating surface 15 against which the container rim seats in positive fashion when the closure and container are assembled together. This seating surface is formed on the lower surface of the base of the 'U', extends in a plane substantially normal to the axis of symmetry of the closure, and is contiguous with and radially outwards of the opening 10 of the recess.

The container 1 comprises a side wall 16 which tapers downwardly from a rim 17. The rim 17 is formed with a radially outwardly projecting rim portion 18 which is interconnected with a downwardly depending flange 19 which lies exteriorly of side wall 16 and surrounds the upper portion of the side wall and is provided with two diametrically opposed bail receiving holes 20.

The container is provided with another part of the locking device in the form of a radially outwardly projecting annular rib 21 at the junction of the rim portion 18 with flange 19, the rib 21 having a lower surface 22 to conform to the upper surface 13 of the locking projection 12 of the closure so that one surface engages with the other in the assembled condition of the two components. Immediately below the rib 21 the flange 19 extends downwardly almost entirely in the axial direction only and then extends downwardly with a radially outward component so that space is provided directly beneath the rib 21 to accommodate the locking projection 12.

During assembly of the closure onto the rim of the container, the container rim is located between the two side walls 5 and 6 and the closure is urged downwardly so that the surface 14 of the locking projection engages with an upper convex surface 23 of the rib 21. The locking projection is then flexibly forced over the rib 21 at one position so that it lies beneath the rib with surfaces 22 and 13 in engagement in this one position. By applying pressure progressively around the 'U' shape rim of the closure, i.e. upon the base 7, radially outward flexing of the side wall 6 is caused by sliding movement of the surface 14 of the locking projection around the convex surface 23 of the rib 21. By this means, the locking projection 12 is progressively forced around the rib 21 until it snaps into position beneath the rib thus locating the closure in a closed position upon the container as shown in FIG. 3. As the closure is urged into its closed position, the upper surface of the container rim portion 18 engages with the O-ring seal 11, i.e. that part of the seal which projects from the opening 10, and gradually compresses it by displacing the seal towards the opening. When the closure is in its closed position, the upper surface of the rim portion 18 lies in positive engagement with the container seating surface 15 of the closure and in this position the previously projecting part of the O-ring seal has been flattened so that it lies substantially level with the opening 10 of the recess and provides a substantial area of sealing engagement with the upper surface of the rim portion. This is shown in FIG. 3.

It can thus be seen that a perfectly good seal is obtained with the construction described in the first embodiment between the O-ring seal 11 and the container rim while providing a positive closed position for the closure upon the container which renders the closure immovable upon the container unless steps are taken positively to remove the closure therefrom. While a positive seat is provided between the two components and a satisfactory seal is also obtained, the seal is made possible without undue compression of the resilient seal. In contrast, a mere deflection of the seal is all that is required while the main portion of the seal contained within the recess 9 is in an undeformed and substantially unstressed condition. It follows from this that little or no setting of the seal takes place even after a long period of time when the two components are assembled together so that leakage between the seal and the container is a most unlikely possibility.

In addition, the above described construction of closure has other advantages as follows. When the closure is urged over the container rim, snap action engagement of the closure over the rim is made possible by an opening effect created by movement of the side wall 6 and base 7 about a pivoted position lying in the vicinity of the junction of the base with the wall 5. As the container seating surface is spaced from this pivot position by the recess 9, a clamping action to hold the container in position within the closure rim and effected by a radially inwardly constricting movement of the locking projection 12 places a great deal of force upon the part of the base in the vicinity of the wall 5 whereby a firm pressure is applied to the deformed area of the seal 11 although extreme deformation of the seal cannot take place for the reasons explained above.

What is claimed is:

1. An assembly of closure and container in which the container has a rim and the closure comprises a container closure portion extending across an opening of the container and an annular rim portion surrounding the closure portion, the rim portion having an axial flange and an annular seating surface facing axially along the flange and extending in a plane substantially normal to the axis of symmetry of the closure, the closure and container each comprising parts of an annular locking device, and the closure being sealingly closed upon the container rim with the parts of the locking device cooperating to retain the closure upon the container and holding the container in positive compressive engagement with the closure solely against the seating surface so that the closure forces are transmitted entirely through the seating surface with the closure immovable upon the container, and the container and closure defining between them an annular chamber containing a resilient seal, said chamber being contiguous with the seating surface and the seal being in a partially compressed state and sealingly engaging both the container and the closure.

2. An assembly according to claim 1 wherein the annular chamber is defined partly by an annular recess formed in the closure rim portion, the rim portion defining the recess with an opening which faces axially along the flange, and the resilient seal which, in a normal uncompressed state has a part which projects from the opening, is held with its otherwise projecting part compressed towards the opening by the container rim.

* * * * *